United States Patent
Levy et al.

(10) Patent No.: US 7,125,552 B2
(45) Date of Patent: *Oct. 24, 2006

(54) METHOD FOR HIGH YIELD PURIFICATION OF IMMUNE GLOBULINS FROM BLOOD PLASMA AND BLOOD PLASMA INTERMEDIATES

(75) Inventors: Joshua Levy, North Hollywood, CA (US); Fred Rothstein, Long Beach, CA (US); Bahman Shimiaei, Los Angeles, CA (US)

(73) Assignee: Hemacare Corporation, Woodland Hills, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/129,638

(22) Filed: May 13, 2005

(65) Prior Publication Data

US 2005/0209442 A1    Sep. 22, 2005

Related U.S. Application Data

(63) Continuation of application No. 10/041,950, filed on Oct. 19, 2001, now Pat. No. 6,893,639.

(51) Int. Cl.
    *A61K 39/395* (2006.01)
(52) U.S. Cl. .............. 424/176.1; 424/177.1; 530/390.1
(58) Field of Classification Search ............ 424/176.1, 424/177.1
    See application file for complete search history.

(56) References Cited

U.S. PATENT DOCUMENTS

| | | | |
|---|---|---|---|
| 4,082,734 A | 4/1978 | Stephan | |
| 4,371,520 A | 2/1983 | Uemura et al. | |
| 4,404,131 A | 9/1983 | Schwartz et al. | |
| 4,481,189 A | 11/1984 | Prince | |
| 4,762,714 A | 8/1988 | Mitra et al. | |
| 4,877,866 A | 10/1989 | Rudnick et al. | |
| 4,948,877 A | 8/1990 | Mitra et al. | |
| 5,159,064 A | 10/1992 | Mitra et al. | |
| 5,419,906 A | 5/1995 | Mitra et al. | |
| 5,648,472 A | 7/1997 | Gehringer et al. | |
| 5,886,154 A | 3/1999 | Lebing et al. | |
| 6,093,324 A | 7/2000 | Bertolini et al. | |
| 6,096,872 A | 8/2000 | Van Holten et al. | |
| 6,162,904 A | 12/2000 | Mamidi et al. | |
| 6,307,028 B1 | 10/2001 | Lebing et al. | |

FOREIGN PATENT DOCUMENTS

WO    WO 99/33484    7/1999

OTHER PUBLICATIONS

L. Martinache and M. P. Henon: "Concentration and Desalting by Ultrafiltration." Methods Plasma Protein Fractionation, 1980, pp. 223-235, PCT.

K. Tanaka, E. Sawtani, G. A. Dias, E. M. Shigueoka, T.C.X.B. Campos, H.C. Nakao and F. Arashiro, "High Quality Human Immunoglobulin G Purified from Cohn Franctions by Liquid Chromatography." Brazilian Journal of Medical and Biological Research, Jan. 2000, vol. 33, No. 1, pp. 27-30, Sao Paulo, SP, Brasil.

*Primary Examiner*—Christina Chan
*Assistant Examiner*—Yunsoo Kim
(74) *Attorney, Agent, or Firm*—Fulwider Patton LLP

(57) ABSTRACT

The method for immune serum globulin purification relates to the purification of immune globulins from blood plasma with a high degree of efficiency and a high rate of recovery. The immune globulin source is Cohn's fraction I+II+III or II+III prepared from plasma or plasma intermediates by precipitation of the paste at pH 6.7 to 6.8 in the presence of 20% ethanol and 80% purified water. A glycine extraction is followed by an anion exchange chromatography column step to achieve a significantly high yield and high purity of the concentrated protein.

10 Claims, 1 Drawing Sheet

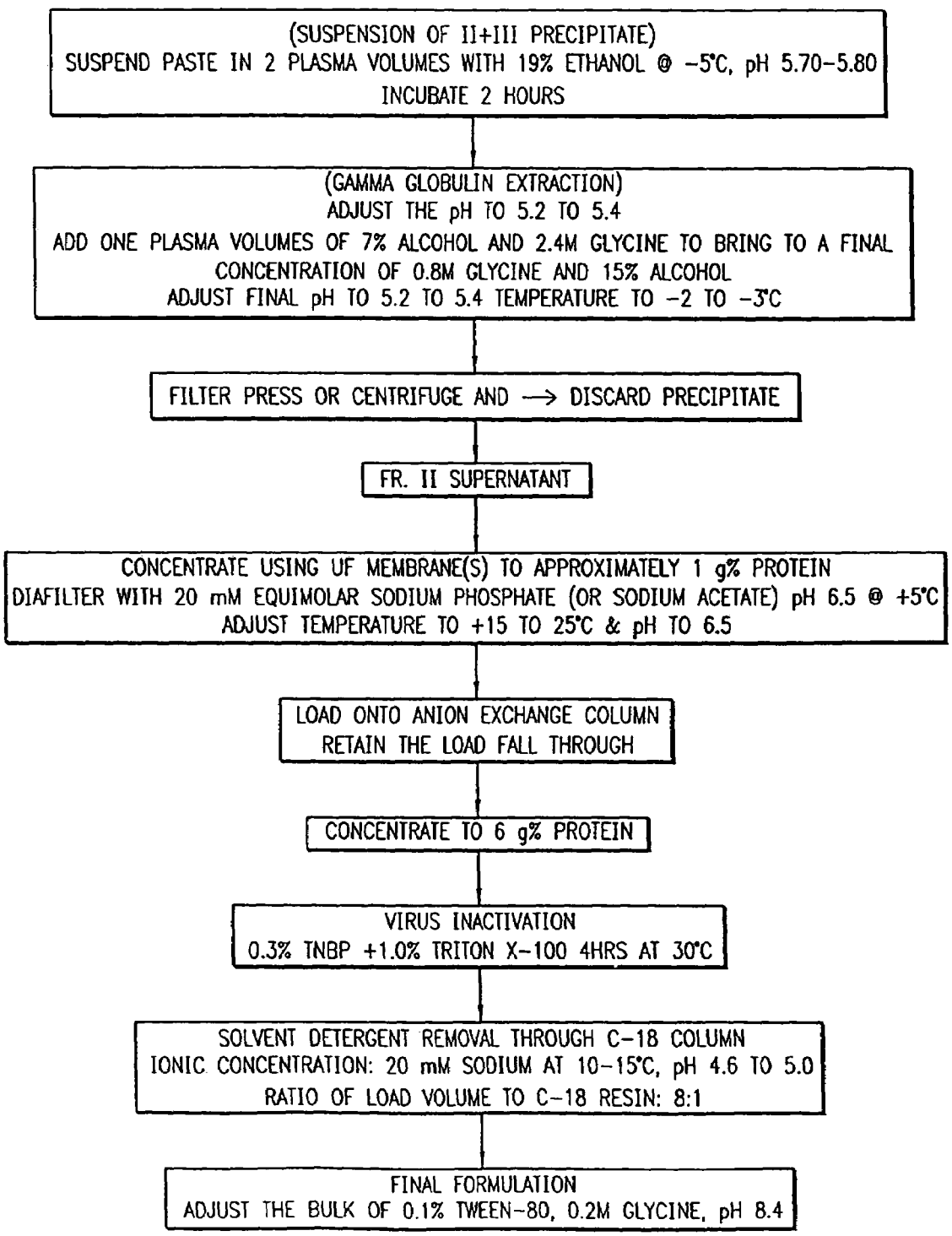

METHOD FOR HIGH YIELD PURIFICATION OF IMMUNE GLOBULINS FROM BLOOD PLASMA AND BLOOD PLASMA INTERMEDIATES

RELATED APPLICATIONS

This is a continuation of Ser. No. 10/041,950, filed Oct. 19, 2001, now U.S. Pat. No. 6,893,639.

BACKGROUND OF THE INVENTION

This invention relates generally to immune serum globulin purification, and more particularly concerns a method of purification of immune globulins from blood plasma with a high degree of efficiency and a high rate of recovery.

Blood plasma proteins have been purified for their therapeutic values for several decades. The most popular method of protein purification with wide industrial application was invented by Dr. Edwin J. Cohn. Dr. Cohn's method uses cold alcohol fractionation to separate major protein components of plasma. With the advent of new technologies, the present invention significantly improves on the recovery and purity of proteins from blood plasma.

It is desirable to provide a method for producing a higher yield of purified immune globulins from blood plasma, with fewer process steps and an increased recovery of the final product. The reduction in the number of process steps and duration of processing will further assure the structural integrity of the original molecules as the native proteins. The present invention meets these needs and others.

SUMMARY OF THE INVENTION

Briefly, and in general terms, the present invention provides a method for purification of immune globulins from blood plasma with a high degree of efficiency and a high rate of recovery. The method of the present invention differs from prior protein purification/recovery methods in that it combines a glycine extraction followed by an anion exchange chromatography column step to achieve a significantly high yield and high purity of the concentrated protein.

The invention is directed to a method for producing a high yield of purified immune globulins from blood plasma. In a preferred embodiment, the method involves suspension of blood product intermediates or another biologic source containing immune globulins (or antibodies) in a solution containing about 20% ethanol and about 80% distilled water (volume/volume) with pH adjusted to between 5.7 and 5.8 and a temperature of about −5° C. The suspension is either precipitated to remove the lipid-containing supernatant (or filtrate) or is incubated at the said temperature before proceeding to the next step. The precipitate or the suspension is then brought to a concentration of 15% ethanol (volume/volume) and about 0.8M glycine at pH 5.2 to 5.4 and at a temperature of approximately −3° C. The solution is incubated at the above conditions to facilitate the extraction of immune globulins (or antibodies) by the glycine solution. Liquid-solid separation is performed to extract the immune globulins in the liquid phase. The liquid phase is then concentrated and solvent-exchange is performed to reduce the glycine and alcohol content. The protein solution is then loaded onto an anion exchange column to bind and reduce any protein impurities. The column flow-through that contains the immune globulins (or antibodies) is then concentrated to approximately 6% protein content. The inactivation of viruses which may be present in the concentrated protein solution is performed by a method of choice. The preferred method of viral inactivation is the solvent-detergent method in accordance with U.S. Pat. No. 4,481,189 (Prince). The solvent-detergent is removed from the protein solution by adsorption onto a C-18 resin column. The collected protein is formulated for final use in a liquid or as a freeze-dried preparation. Preferably, the collected protein is in the liquid formulation wherein the final concentration is adjusted to approximately 5.0 to 10.0 grams/deciliter protein, in 0.1% Tween-80, 0.2M glycine and pH between 8.2 and 8.6.

These and other aspects and advantages of the invention will become apparent from the following detailed description, which illustrates by way of example the features of the invention.

BRIEF DESCRIPTION OF THE DRAWINGS

FIG. 1 is a flow-chart of a method for high yield purification of immune globulins from blood plasma in accordance with the present invention.

DETAILED DESCRIPTION OF THE PREFERRED EMBODIMENTS

This improved method of the present invention ensures a high yield and high purity preparation of immune globulins from human plasma or similar immune globulin sources. The overall recovery of immune globulins from Cohn fraction II+III or I+II+III is about 80% with a purity of 99% or more as measured by zone electrophoresis. The final product of the concentrated protein is stable and has low anti-complement activity.

The conventional industrial methods of immune globulins purification from blood plasma are based on cold ethanol fractionation which co-precipitated groups of proteins based on their isoelectric points at given alcohol concentrations at sub-zero temperatures. Use of the glycine extraction method in the present invention, followed by chromatographic separation, combines the benefits of a crude protein cut, followed by a specific purification over the chromatography column.

In a preferred embodiment, the immune globulin source is Cohn's fraction I+II+III or II+III prepared from plasma or plasma intermediates by precipitation of the paste at pH 5.7 to 5.8 in the presence of 20% ethanol and 80% purified water. As shown in FIG. 1, the immune globulin (or antibody) source, Cohn's fraction I+II+III or II+III, is suspended in a solution consisting of about 19% ethanol and about 81% purified water at a volume equivalent to two times that of the initial source at a temperature in a range of about −4° C. to about −6° C. with vigorous agitation. It is preferred that the immune globulin suspension is prepared at a temperature of approximately −5° C. Alternative sources of immune globulins or antibodies can be derived from non-human sources such as those from tissue culture or animal origin for use in the present invention.

The precipitation of a majority of phospholipids from the immune globulin suspension is activated by adjusting the pH of the suspension to approximately 5.7 to 5.8 using 1.0M sodium acetate (or 4.0M sodium acetate for less volume) while continuously agitating the suspension. The suspension is incubated for a minimum of two hours at a temperature in a range of about −4° C. to about −6° C. with moderate agitation. Alternatively, liquid-separation of the suspension can be performed at this step in the process, rather than incubation of the suspension, followed by repetition of the earlier steps of preparing the suspension and precipitating the same.

Following the incubation period of the immune globulin suspension, a volume of a solution of 2.4M glycine in 7% ethanol and purified water (volume/volume), equivalent to the volume of the initial plasma source, is added to the suspension with vigorous mixing. Preferably, the final concentration of alcohol in the suspension is 15% (volume/volume) and the final concentration of glycine in the suspension is 0.8M. In order to have a better separation and higher yield, the volume of the suspension can be increased to a volume equivalent to five times the volume of the initial plasma source while maintaining the ethanol and glycine at 15% and 0.8M respectively. The pH of the suspension is then preferably adjusted to about 5.2 to about 5.4 using a buffer of 1.0M to 4.0M sodium acetate. The suspension temperature is raised to approximately −2° C. to −3° C.

The preferred technique for this separation is by use of a filter press. Filtration is facilitated with the use of diatomaceous earth at a concentration in a range of about 1% to 3% (weight/volume).

The filtrate or the centrifugate is then concentrated preferably by ultrafiltration to approximately 1.0 gram/deciliter protein content at a temperature in a range of about −2° C. to about −3° C. with moderate agitation. Ultrafiltration of the filtrate or the centrifugate containing the immune globulins is performed preferably by using a 100,000 molecular weight cut-off ultrafilter membrane to concentrate the protein to approximately 1 g %.

In order to reduce the glycine and alcohol content of the protein concentrate, solvent-exchange is performed using a solution of 20 mM sodium phosphate at a pH of about 6.5 and a temperature of about 5° C. The solution is prepared by a mixture of sodium phosphate monobasic and sodium phosphate dibasic at a ratio that yields a pH of about 6.5. Alternatively, a buffer consisting of 20 mM sodium acetate at a pH of about 6.5 can be used in the present invention. Solvent-exchange is performed by adding one volume of the pH 6.5 buffer to the protein concentrate and concentrating the new solution to its original volume. The solvent-exchange procedure is performed at least four times in order to ensure a reduction in the alcohol and glycine content of the protein concentrate. Following the last solvent-exchange, the temperature of the protein solution is raised to room temperature (15° C. to 25° C.).

The protein solution is then preferably passed through an anion exchange chromatography column to remove any impurities such as IgA, IgM, albumin and other protein impurities. Examples of the type of gel (resin) that can be used in the present invention to achieve satisfactory purification results includes a Pharmacia Q-Sepharose gel (resin). The column is equilibrated with the same 20 mM, pH 6.5 buffer that was used for solvent-exchange. The column is post-washed with one to two column volumes of the 20 mM, pH 6.5 buffer for any further recovery of protein. The ratio of the protein to the gel is approximately 0.4 grams of protein/milliliter of packed gel. The column effluent that contains the purified immune globulins or antibodies is concentrated by ultrafiltration to approximately 6 grams/deciliter protein content (6 g %) using a 100,000 molecular weight cut-off ultrafilter membrane.

After concentrating the column effluent by ultrafiltration, viral inactivation is performed on the concentrated protein solution. A preferred method of viral inactivation is the solvent-detergent method in accordance with U.S. Pat. No. 4,481,189 (Prince). The mixture of the solvent-detergent and protein concentrate consists of a final concentration of 0.3% TNBP (tri-n-butyl phosphate) and 1.0% Triton-X-100 and is then incubated for approximately four hours at 30° C.

Following incubation of the combined protein concentrate and solvent-detergent mixture, the solvent-detergent is removed from the protein solution by adsorption onto a C-18 resin. The pH of the protein solution is then adjusted to about 4.6 to about 5.0 using a buffer of 4.0M sodium acetate. The column containing the C-18 resin is equilibrated with a 20 mM acetate buffer at a pH in a range of about 4.6 to about 5.0. The protein solution is loaded onto and passed through the column in order to remove the remaining solvent-detergent from the viral inactivation procedure. The ratio of the load volume to the resin volume is approximately eight parts load volume to one part C-18 resin.

The collected protein from the column is formulated for final use either in a liquid or as a freeze-dried preparation. Preferably, the final product is in a liquid formulation having a concentration of approximately 5.0 to 10.0 grams/deciliter protein, 0.1% polysorbate-80 (Tween-80), 0.2M glycine and a pH in a range of about 8.2 to about 8.6.

It will be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. A method for producing a high yield of purified immune globulins, comprising:
   suspending immune globulins in an ethanol solution;
   adjusting the pH of the suspension to about 5.7 to 5.8;
   incubating the suspension for at least two hours;
   adding a solution of glycine, ethanol and water to the suspension;
   adjusting the pH of the suspension to about 5.2 to 5.4;
   extracting the immune globulins from the suspension in a liquid phase to provide an extract containing immune globulins;
   concentrating the extract containing immune globulins, and removing any impurities from the extract containing immune globulins using an anion exchange chromatography column to provide a purified extract solution containing immune globulins;
   concentrating the purified extract solution containing immune globulins to provide a concentrated purified extract solution containing immune globulins;
   treating the concentrated purified extract solution containing immune globulins with a solvent-detergent mixture to inactivate viruses, and removing the solvent-detergent mixture from the concentrated purified extract solution containing immune globulins; and
   formulating the concentrated purified extract solution containing immune globulins for final use.

2. The method of claim 1, wherein the ethanol solution is comprised of about 19% ethanol and about 81% purified water.

3. The method of claim 1, wherein the step of suspending the immune globulins in the ethanol solution occurs at a temperature of about −5° C.

4. The method of claim 1, wherein the step of adding the solution of glycine, ethanol and water to the suspension comprises producing a final concentration of glycine in the suspension of about 0.8M and a final concentration of ethanol in the suspension of about 15% (volume/volume).

5. The method of claim 1, wherein the step of extracting the immune globulins from the suspension is performed by one of centrifugation and filtration.

6. The method of claim 1, wherein the step of extracting the immune globulins from the suspension is performed by use of a filter press.

7. The method of claim 1, wherein the step of extracting the immune globulins from the suspension is facilitated using diatomaceous earth at a concentration of about 1% to about 3% weight by volume during filtration.

8. The method of claim 1, wherein the extract containing immune globulins is concentrated through an ultrafiltration membrane.

9. The method of claim 1, wherein the purified extract solution containing immune globulins is concentrated using an ultrafiltration membrane.

10. The method of claim 1, wherein the concentrated purified extract solution containing immune globulins is formulated for final use in one of a liquid and a freeze-dried preparation.

* * * * *